United States Patent [19]

Murakoshi

[11] Patent Number: 5,217,618
[45] Date of Patent: Jun. 8, 1993

[54] PLASMA PURIFICATION TREATMENT

[75] Inventor: Masahide Murakoshi, Nakaimachi, Japan

[73] Assignee: Terumo Kabushiki Kaisha, Tokyo, Japan

[21] Appl. No.: 749,561

[22] Filed: Aug. 26, 1991

[51] Int. Cl.$^5$ .............................................. B01D 61/00
[52] U.S. Cl. ..................... 210/647; 210/645; 210/649; 210/767; 210/805; 210/806; 210/929; 422/1; 422/41; 604/4; 604/5; 604/6
[58] Field of Search ............... 210/646, 649, 647, 650, 210/651, 767, 782, 787, 789, 806, 805, 929, 645; 604/4, 5, 6, 406, 408, 409, 410; 424/530; 422/3, 1, 41, 44

[56] References Cited

U.S. PATENT DOCUMENTS

| | | | |
|---|---|---|---|
| Re. 33,924 | 5/1992 | Valeri | 210/782 |
| 4,047,526 | 9/1977 | Reynolds et al. | 604/4 |
| 4,086,924 | 5/1978 | Latham, Jr. | 604/6 |
| 4,223,672 | 9/1980 | Terman et al. | 210/782 |
| 4,321,192 | 3/1982 | Jain | 604/6 |
| 4,350,156 | 9/1982 | Malchesky et al. | 604/28 |
| 4,814,077 | 3/1989 | Furuyoshi et al. | 210/679 |
| 4,954,128 | 9/1990 | Ford | 604/5 |
| 4,994,021 | 2/1991 | Smith et al. | 604/6 |

FOREIGN PATENT DOCUMENTS

1-249062 10/1989 Japan ........................... 604/5

Primary Examiner—Robert A. Dawson
Assistant Examiner—Sun Uk Kim
Attorney, Agent, or Firm—Frishauf, Holtz, Goodman & Woodward

[57] ABSTRACT

A plasma purification treatment which removes disease ailment causing constituents in the plasma of a patient suffering from diseases caused by those ailment causing constituents in this patient's plasma by plasma exchange made by sampling of plasma from the patient and returning the plasma sampled from the patient and purified by removing the ailment causing constituents to the patient; sampling an appropriate volume of plasma within 12% of the patient's whole circulating blood at the first time and gradually increased volume from the second time on until it reaches a predetermined target volume of plasma exchange, returning the sampled plasma at the previous time and purified.

23 Claims, 5 Drawing Sheets

PLASMA PURIFICATION TREATMENT

BACKGROUND OF THE INVENTION

The present invention relates to a plasma purification treatment or a plasma purification therapy which removes disease-causing constituents from the plasma of a patient suffering from diseases caused by those ailment causing constituents in his or her blood plasma.

Contained in human plasma are various proteins such as albumin, immunoglobulins (IgG, IgA, IgM) and fibrinogen and other constituents such as nucleic acid and lipids. Although their concentrations are controlled by the various mechanisms of the living body so as to maintain the balance of each system which they belong to, the balance of some system can be disturbed from internal or external causes, resulting in an abnormal increase or presence of particular constituents. This abnormal increase or presence of plasma constituents is known to cause various diseases.

Known as such type of diseases are immunologically caused kidney diseases (acute renal transplant rejection, GOODPASTURE syndrome, etc.), collagen diseases (chronic rheumatoid arthritis, systemic lupus erythematosus, myasthenica gravis, Graves disease, autoimmune hemolytic anemia, Sjoegren syndrome, etc.), plasma proteins abnormality diseases (multiple myeloma, primary macrogrobulinemia, etc.), cholesterol (low-density lipoprotein in particular) metabolic error disease (familial cholesterolemia), liver diseases (bilirubinemia, etc.), and poisonings.

Recently, so called plasma exchange therapy which removes plasma from a patient and returns fresh or frozen plasma or albumin preparation to the patient for replenishment has been applied to clinical treatment and its therapeutic value has been confirmed. However, this plasma exchange therapy has a problem that it needs a large volume of substitute liquid to exchange with the plasma of a patient. Further, when an albumin preparation is used as the replacement liquid, all the necessary constituents of plasma cannot be supplied. On the other hand, when fresh or frozen plasma is used as the substitute liquid, since it is prepared using plasma of donors, there is a high risk of infection of hepatitis and acquired immunodeficiency syndrome (AIDS) and of outbreak of allergy.

To solve the above problems, a plasma purification treatment has been proposed which removes disease-causing constituents alone from the plasma of a patient and returns the treated plasma to the patient. This plasma purification treatment draws blood from a patient by means of a pump or other appropriate means at the rate of about 100 ml per minute, separates the plasma and the blood cells of the whole blood by a centrifuge or membrane filters, removes the causative constituents from the plasma, joins the treated plasma and the blood cells together, then returns the blood back to the patient. There are several methods for removing causative constituents from plasma: salting-out method which adds salting-out agents to plasma and precipitates causative constituents (for example, high-molecular weight proteins) by the difference of solubility (U.S. Pat. No. 4,321,192); adsorbing method which adsorbs causative constituents using adsorbents with specific adsorbing capability to them (U.S. Pat. No. 4,814,077); cooling-out method which cools plasma and precipitates causative constituents (U.S. Pat. No. 4,350,156); filtering method which removes causative constituents by means of filters which retain causative constituents and larger molecular weight constituents (U.S. Pat. No. 4,350,156).

Purification of plasma by these method in which blood is circulated in an extracorporeal circuit through the processing steps has problems as described below.

Problems due to the limitation on the volume of blood circulated in an extracorporeal circuit This on-line plasma purification method requires a large volume of extracorporeal blood circulation, because it carries out separation of plasma from blood cells and removal of disease-causing constituents from the plasma in a continuous process simultaneously. A large volume of extracorporeal blood circulation can cause low blood pressure, slow pulse, or disequilibrium syndrome to the patient. To increase the effectiveness of this method, it is necessary to increase the capacity of the means for removing causative constituents from plasma. This can be attained by increasing the size of the adsorbent canister and hence the amount of adsorbent accommodated for the adsorbing method or by increasing the area of the filters for other methods. However, improvement of the disease-causing constituents removing capability of these methods is limited, because they further increase the volume of blood circulated in the extracorporeal circuit.

Problems due to extracorporeal blood circulation

Since the above on-line plasma purification method separates plasma from whole blood and then purifies the plasma in a continuous process while the blood of a patient is being circulated through an extracorporeal circuit, if some trouble happens with the means for separating plasma or that for purifying the separated plasma, the patient is kept waiting in the middle of treatment until the trouble is corrected. Moreover, when the cause of the trouble is a clogged filter, for instance, it is difficult to return the plasma in the extracorporeal circuit to the patient. To prevent such an accident, extracorporeal blood circulation systems used for the plasma purification system must be provided with a monitoring means for maintaining the safety of patients and which detects bubbles, dissolution of erythrocyte, pressure (arterial pressure, venous pressure, filtering pressure, etc.), electrical conductivity and temperature (whole blood, plasma, etc.) and controls the system automatically according to the signals from the detectors. Thus, they become bulky and complicated, causing problems with their installation space (particularly at bedside) and difficult training for operating them.

Problem of the time taken for treatment

It takes about two hours to treat the whole plasma of a patient when circulating blood at the flow rate of 100 ml/min. and treating plasma at the rate of 20 ml/min. with an additional time required to return the blood and the plasma in the extracorporeal circuit back to the patient. Therefore, the patient must be put under restraint for such a long time.

SUMMARY OF THE INVENTION

The object of this invention is to provide a plasma purification clinical treatment or a plasma purification therapy which can solve the above problems and does not need any replenishing substitutes for plasma constituents such as albumin.

The above object is attained by the plasma purification treatment of the present invention as described below.

The first plasma purification treatment according to the present invention of the type wherein blood is drawn from a patient, the blood is separated into plasma and concentrated cellular elements, the concentrated cellular elements are returned to the patient, the plasma is treated to remove ailment causing constituents and thereafter the treated plasma is returned to the patient;

the improvement wherein an increased volume of plasma becomes available for the extracorporeal plasma treatment;

comprising the steps, (a) sampling a first sample of plasma from the patient, said sample of the plasma having a first volume which is up to about 12% of the total volume of blood circulating in the patient, and storing the first sample of the plasma, under conditions to preserve its properties; thereafter (b) waiting a time sufficient for the patient's body to replace substantially the sampled plasma; thereafter (c) returning the first sample of plasma to the patient and taking a second sample of plasma having a second volume which is equal to the sum of the first volume and an additional amount of up to 12% of the volume of blood circulating in the patient; whereby the second volume of the plasma is available as an extracorporeal supply.

The second plasma purification treatment

In extracorporeal plasma purification treatment of the type wherein blood is drawn from a patient, the blood is separated into plasma and concentrated cellular elements, the concentrated cellular elements are returned to the patient, the plasma treated to remove ailment causing constituents and thereafter the treated plasma is returned to the patient;

the improvement wherein an increased volume of plasma becomes available for the extracorporeal plasma treatment;

comprising the steps, (a) sampling a first sample of plasma from the patient, said sample of the plasma having a first volume which is up to about 12% of the total volume of blood circulating in the patient, and storing the first sample of plasma, under conditions to preserve its properties; thereafter (b) waiting a time sufficient for the patient's body to replace substantially the sampled plasma; thereafter (c) sampling a second sample of plasma from the patient, said sample of the plasma having a volume which is up to about 12% of the total volume of blood circulating in the patient, and storing the second sample of plasma, under conditions to preserve its properties; thereafter (d) the steps of the sampling, storing and waiting are continued until a predetermined target volume of the plasma is sampled from the patient (e) returning the sampled and preserved plasma to the patient and taking the target volume of the plasma is available as an extracorporeal supply.

DETAILED DESCRIPTION OF THE PREFERRED EMBODIMENTS

The plasma purification treatment of the present invention is described below with reference to the drawings.

In extracorporeal plasma purification treatment of the type wherein blood is drawn from a patient, the blood is separated into plasma and concentrated cellular elements, the concentrated cellular elements are returned to the patient, the plasma treated to remove ailment causing constituents and thereafter the treated plasma is returned to the patient;

The improvement wherein an increased volume of plasma becomes available for the extracorporeal plasma treatment;

comprising the steps, (a) sampling a first sample of plasma from the patient, said sample of the plasma having a first volume which is up to about 12% of the total volume of blood circulating in the patient, and storing the first sample of the plasma, under conditions to preserve its properties; thereafter (b) waiting a time sufficient for the patient's body to replace substantially the sampled plasma; thereafter (c) returning the first sample of plasma to the patient and taking a second sample of plasma having a second volume which is equal to the sum of the first volume and an additional amount of up to 12% of the volume of blood circulating in the patient; whereby the second volume of the plasma is available as an extracorporeal supply.

Here "remove ailment causing constituents" means not only complete removal of ailment causing constituents", but partial removal of them.

Figure 1:
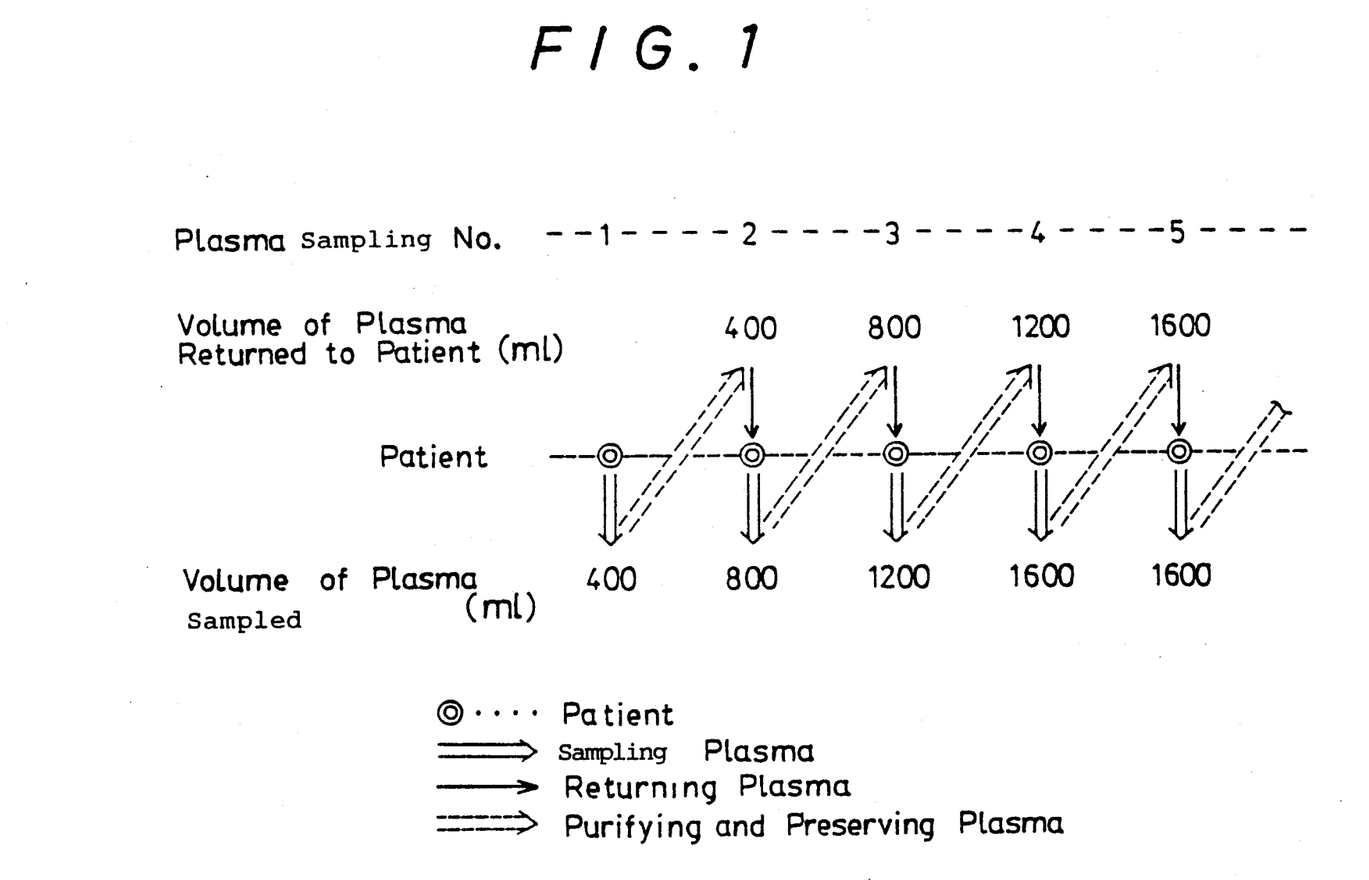
FIG. 1 is a diagram to illustrate an embodiment of the first plasma purification treatment according to the present invention.

Hereinafter described is an embodiment of the first plasma purification treatment according to the present invention referring to FIG. 1.

When applying this first plasma purification treatment according to the present invention to a patient, a target volume of plasma exchange is determined before starting treatment taking into consideration the weight, age, and disease state of the patient, causative constituents, concentrations of the causative constituents, and so on. Thereafter, an appropriate volume of plasma within 12% of the patient's whole circulating blood, 400 ml in this embodiment, is sampled from the patient into a sterile container as the first sampling. If the volume of plasma sampled by one sampling is within 12% of the patient's whole circulating blood, there is no risk of low blood pressure, slow pulse, or imbalance syndrome caused by sampling of a large volume of plasma. The first sampling of plasma is only this sampling of plasma and therefore the patient has to be put under restraint only for the time necessary for sampling plasma.

Blood is drawn from the patient, the blood is separated into plasma and concentrated cellular elements by conventional methods such as centrifugation with a centrifuge or filtration with membrane filter.

The sampled plasma is purified by removing ailment causing constituents using appropriate methods according to the ailment causing constituents.

To preserve the sampled plasma and the purified plasma, it is preferable to cool them below 4° C. This cold preservation prevents the denaturation and loss of activity of plasma components. Frozen preservation is more preferable for cold preservation. When the purification process is salting out as described below and the purified plasma is preserved with salting-out agents such as NaCl, it is possible to preserve the purified plasma above 4° C.

Ailment causing constituents in plasma can be removed by several methods such as salting-out method which adds salting-out agents to plasma and precipitates high-molecular weight proteins by the difference of solubility (U.S. Pat. No. 4,321,192); adsorbing method which adsorbs causative constituents using adsorbents with specific adsorbing capability to them (U.S. Pat. No. 4,814,077); cooling-out method which cools plasma and precipitates ailment causing constituents (U.S. Pat. No. 4,350,156); filtering method which filtrates ailment causing constituents by means of filters which retain causative constituents and larger molecular weight constituents (U.S. Pat. No. 4,350,156), and their combinations.

The second sampling of plasma is conducted after a certain period, 2 to 30 days, for example, from the first drawing of plasma. The certain period is preferably three days up to thirty days, more preferably at least one week. An increased volume of plasma is sampled by the second sampling. The increment is preferably within 12% of the patient's whole circulating blood for the same reason as for the first sampling of plasma. In this embodiment, the volume is increased by 400 ml as shown in FIG. 1 and 800 ml of plasma is sampled from the patient. At the same time, the plasma which was sampled at the first sampling of plasma and purified is returned to the patient. As shown in FIG. 1, plasma exchange made by this sampling of plasma and returning of the sampled plasma at the previous time and purified are repeated from the third sampling of plasma on, increasing the volume of plasma sampled each time as at the second sampling of plasma, until the sampling volume of plasma at one time reaches a target volume of plasma, for example, 1600 ml. The target volume of plasma exchange are determined properly according to the concentrations of ailment causing constituents of the patient plasma. The intervals between the treatments from the third sampling of plasma are determined properly according to the condition of the patient, the sampling volume of plasma, the concentrations of ailment causing constituents of patient plasma, the recovery of plasma products other than constituents, and so on. When a large volume of plasma is exchanged, the interval is preferably longer than a week because the level of the concentrations of plasma components other than causative constituents also decreases considerably.

The increment of sampling volume of plasma from the third time on is not required to be same, but may also be changed according to the patient's condition. Further, the volume of purified plasma returned to the patient may be adjusted according to the condition of the patient as well.

Hereinafter described is an example of the present invention referring to FIG. 1.

Figure 4:
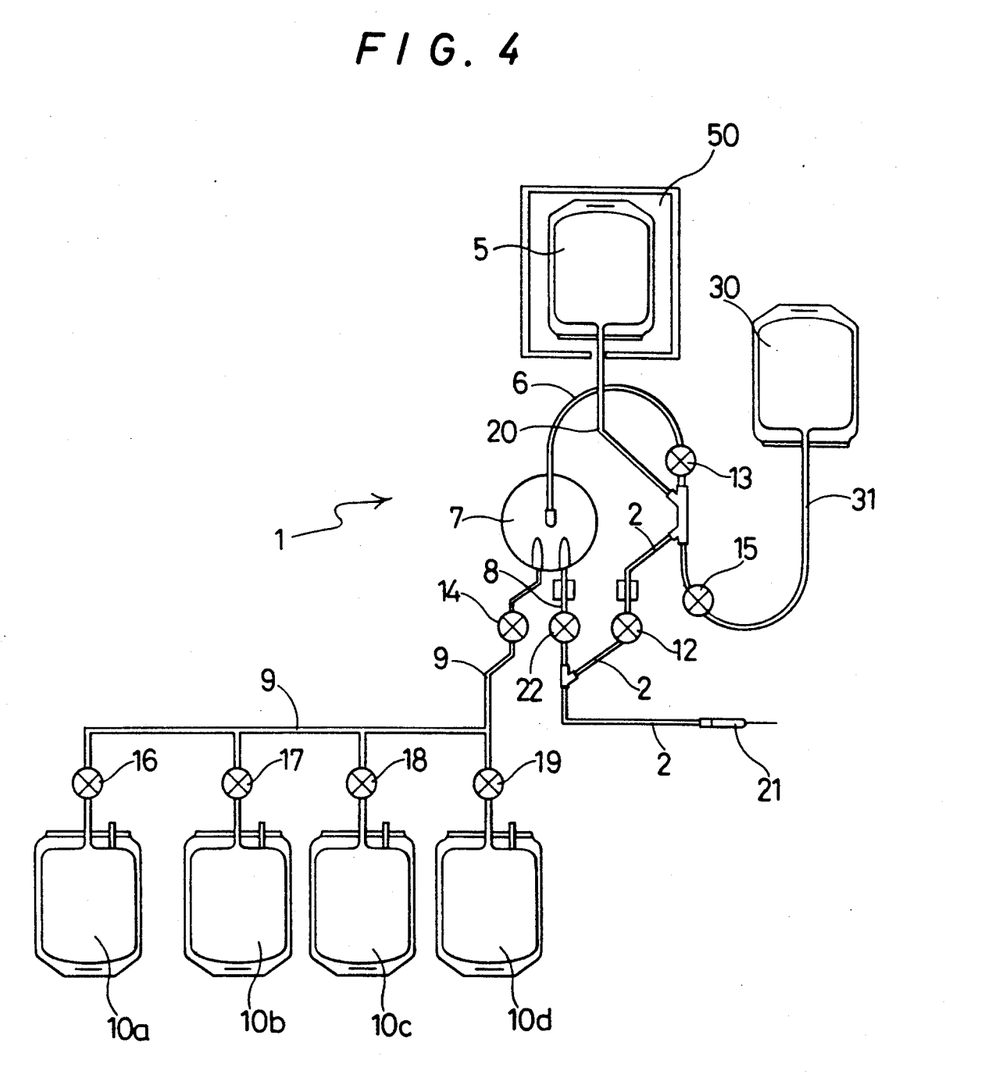
FIG. 4 is a schematic illustration of a plasma collecting circuit.

Plasma is collected by a plasma collecting circuit shown in FIG. 4 and a plasma collecting apparatus (not shown).

The plasma collecting circuit 1 comprises a blood collection needle 21, a blood collection bag 5 (400 ml volume) having a tube 20, a first blood transportation tube 2 which connects the blood collection needle 21 to the tube 20 of the blood collection bag 5, a blood separator 7, a second blood transportation tube 6 which connects the tube 20 of the blood collection bag 5 to the blood separator 7, a third blood transportation tube 8 connecting a blood outlet of the blood separator 7 to the first blood transportation tube 2, four plasma collection bags 10a, 10b, 10c, 10d containing salting-out agent such as NaOH, the plasma transportation tube 9 which connects a plasma outlet of the blood separator 7 to these plasma collection bags, an anticoagulant liquid container 30 and an anticoagulant liquid transportation tube 31 which connects the anticoagulant liquid container 30 to the tube 20 of the blood collection bag 5.

A plasma collection apparatus has a portion 50 which receives the blood collection bag 5, pressurizing and depressurizing means which pressurizes or depressurizes the interior of the portion 50, an attachment which detachably attaches the plasma separator 7, and some shut-off means 12, 13, 14, 15, 16, 17, 18, 19, 22 for closing or opening these tubes of the plasma circuit 1.

The first plasma sampling operation using the plasma collection circuit 1 and the plasma collection apparatus will be described with reference to FIG. 4.

The plasma collection apparatus carries out an anticoagulant liquid injection step that the interior of the portion 50 is depressurized by the operation of the pressurizing and depressurizing means so as to inject a predetermined amount of anticoagulant liquid into the blood collection bag 5 from the anticoagulant liquid container 30.

Next, the plasma collection apparatus carries out a blood collection step that the interior of the portion 50 for the blood collection bag 5 is depressurized by the operation of the pressurizing and depressurizing means so as to collect a predetermined amount of blood (400 ml in this case) into the blood collection bag 5 from patient.

Next, the plasma collection apparatus carries out a small amount blood return step that the interior of the receiving portion 50 for the blood collection bag 5 is pressurized by the operation of the pressurizing and depressurizing means so as to return the blood remaining in the tube 20 of the blood collection bag 5 and in the first blood transportation tube 2 to the patient, and to flow the blood collected in the blood collection bag 5 into the tube 20 of the blood collection bag 5 and into the first blood transportation tube 2.

Next, the plasma collection apparatus carries out a separation and blood return step that the interior of the portion 50 is pressurized by the operation of the pressurizing and depressurizing means so as to flow the blood collected in the blood collection bag 5 into the plasma separator 7, to collect plasma into the plasma collection bag 10a (400 ml volume) from the plasma outlet of the plasma separator 7, and to return blood cell to the patient from the blood cell outlet of the plasma separator 7.

At first, about 200 ml of plasma is sampled into the plasma collection bag 10a. The plasma collection apparatus repeats the above-mentioned anticoagulant liquid injection step, blood collection step, small amount blood return step and separation and blood return step. Hereby, about 400 ml of plasma is collected into the plasma collection bag 10a shown in FIG. 1. The plasma collection bag 10a is cut off from the plasma collecting circuit 1. The collected plasma is mixed with the salting out agent in the plasma collection bag 10a. The collected plasma is preserved below 4° C. Causative constituents such as high molecular weight proteins in plasma is precipitated by the difference of solubility in the plasma collection bag 10a.

Figure 5:
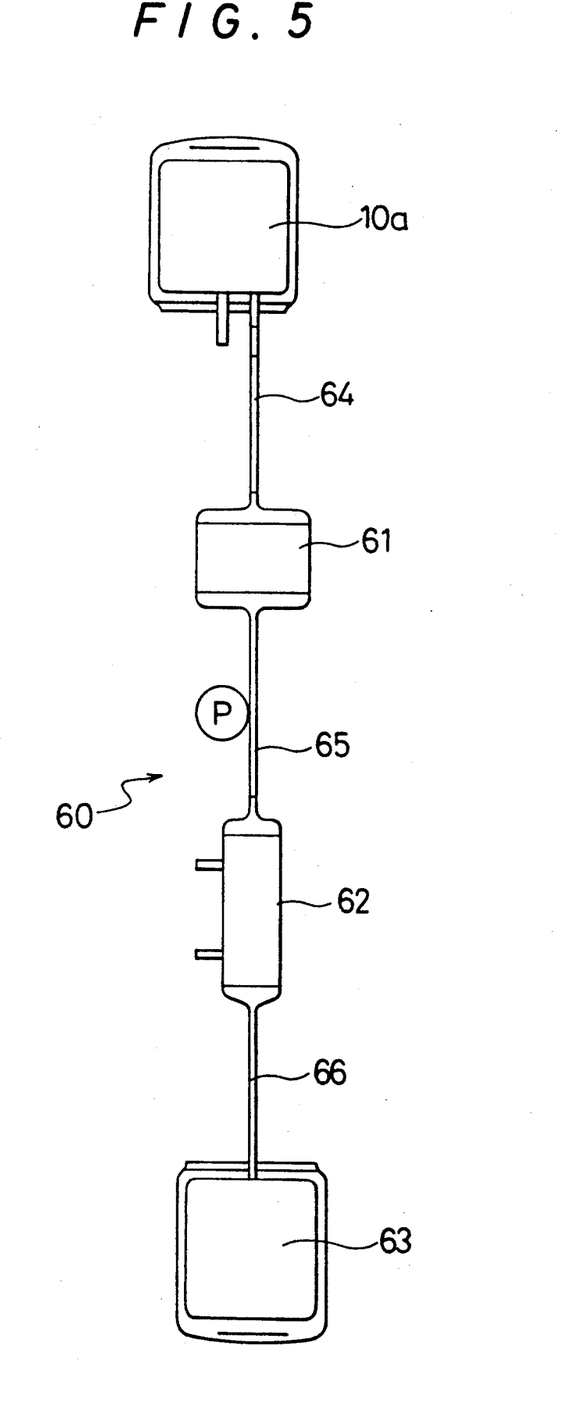
FIG. 5 is a schematic illustration of a plasma treatment apparatus.

Before the second sampling of plasma, the collected plasma in the plasma collection bag 10a is treated by a plasma treatment apparatus shown in FIG. 5.

The plasma treatment apparatus 60 comprises a filter 61 to trap precipitated ailment causing constituents in the collected plasma, a dialyzer 62 to remove the salting out agent such as NaCl and to adjust electrolytes of plasma and a treated plasma collection bag 63 to collect treated plasma. A tube 64 connects an inlet of the filter 61 to the plasma collection bag 10a. A tube 65 connects an inlet of the dialyzer 62 to an outlet of the filter 61. A tube 66 connects the treated plasma collection bag 63 to an outlet of the dialyzer 62.

The second sampling of plasma is conducted after a certain period, for example at least three days, preferably at least one week, from the first sampling of plasma.

In this example of the invention, 800 ml of plasma is sampled from the patient at the second sampling of plasma. At the same time, the above treated plasma (about 400 ml) is returned to the same patient. The second drawing of plasma can be conducted by the above mentioned plasma collecting circuit 1 and plasma collecting apparatus.

At first about 400 ml of plasma is collected into the plasma collection bag 10a, and then about 400 ml of plasma is collected into the plasma collection bag 10b. Hereby, about 800 ml of plasma is collected.

The third sampling of plasma is conducted after a certain period, for example at least three days, preferably at least one week, from the second drawing of plasma.

Before the third sampling of plasma, the collected plasma in the plasma collection bags 10a and 10b is treated by the plasma treatment apparatus 60.

In this example of the invention, 1200 ml of plasma is sampled from the patient at the third sampling of plasma. At the same time, the above treated plasma (about 800 ml) is returned to the same patient. The third sampling of plasma can be conducted by the above mentioned plasma collecting circuit 1 and plasma collecting apparatus.

At first, about 400 ml of plasma is collected into the plasma collection bag 10a, then about 400 ml of plasma is collected into the plasma collection bag 10b and then about 400 ml of plasma is collected into the plasma collection bag 10c. Hereby, about 1200 ml of plasma is collected.

The fourth sampling of plasma is conducted after a certain period, for example at least three days, preferably at least one week, from the third drawing of plasma.

Before the fourth sampling of plasma, the collected plasma in the plasma collection bags 10a, 10b and 10c is treated by the plasma treatment apparatus.

In this example of the invention, 1600 ml of plasma is sampled from the patient at the fourth drawing of plasma. At the same time, the above treated plasma (about 1200 ml) is returned to the same patient. The fourth sampling of plasma can be conducted by the above mentioned plasma collecting circuit 1 and plasma collecting apparatus.

At first about 400 ml of plasma is collected into the plasma collection bag 10a, then about 400 ml of plasma is collected into the plasma collection bag 10b, then about 400 ml of plasma is collected into the plasma collection bag 10c and then about 400 ml of plasma is collected into the plasma collection bag 10d. Hereby, about 1600 ml of plasma is collected. 1600 ml of plasma is a predetermined target volume of plasma exchange.

The fifth sampling of plasma is conducted after a certain period, for example at least three days, preferably at least one week, from the fourth sampling of plasma.

Before the fifth sampling of plasma, the collected plasma in the plasma collection bags 10a, 10b, 10c and 10d is treated by the plasma treatment apparatus.

1600 ml of plasma is sampled from the patient at the fifth sampling of plasma. At the same time, the above treated plasma (about 1600 ml) is returned to the same patient. The fifth sampling of plasma can be conducted by the above mentioned plasma collecting circuit 1 and plasma collecting apparatus.

At first about 400 ml of plasma is collected into the plasma collection bag 10a, then about 400 ml of plasma is collected into the plasma collection bag 10b, then about 400 ml of plasma is collected into the plasma collection bag 10c and then about 400 ml of plasma is collected into the plasma collection bag 10d. Hereby, about 1600 ml of plasma is collected.

After the fifth sampling of plasma, the above treatment and sampling of plasma are repeated as necessary.

Next, another embodiment of the plasma purification treatment according to the present invention is described below referring to FIG. 2.

The plasma purification treatment according to the present invention removes disease ailment causing constituents in the plasma of a patient suffering from diseases caused by those causative constituents in his or her plasma by plasma exchange made by drawing of plasma from the patient and returning the plasma drawn from the patient and purified by removing the ailment causing constituents to the patient: drawing an appropriate volume of plasma within 12% of the patient's whole circulating blood at the first time and gradually increased volume from the second time on, returning the plasma drawn at the previous time without the purification treatment, until it reaches a predetermined target volume of plasma exchange; and after then stopping increasing the volume of plasma drawn to draw said target volume of plasma, returning the plasma drawn at the previous time and purified.

When applying this plasma purification treatment according to the present invention to a patient, a target volume of plasma exchange is determined before starting treatment taking into consideration the weight, age, and disease state of the patient, ailment causing constituents, concentrations of the causative constituents, and so on. Thereafter, an appropriate volume of plasma within 12% of the patient's whole circulating blood, 400 ml in this embodiment, is drawn from the patient into a sterile container as the first drawing.

The first operation is only this drawing of plasma and therefore the patient has to be put under restraint only for the time necessary for drawing plasma.

Plasma is separated from the drawn blood by conventional methods such as centrifugation with a centrifugal or filtration with membrane filter. This plasma is preserved without the purification treatment until the next drawing of plasma by. It is preferably to preserve the plasma cooling below 4° C. This cold preservation prevents the denaturation and loss of activity of plasma components. Frozen preservation is more preferable for cold preservation. Ailment causing constituents in plasma can be removed by the same methods as for the first plasma purification method according to the present invention.

The second drawing of plasma is conducted after a certain period, 2 to 30 days for example, from the first drawing of plasma. An increased volume of plasma is drawn by the second drawing. The increment is preferably within 12% of the patient's whole circulating blood for the same reason as for the first drawing of plasma. In this embodiment, the volume is increased by 400 ml as shown in FIG. 2 and then 800 ml of plasma is drawn from the patient. At the same time, the plasma drawn by the first drawing is returned without the purification treatment. As shown in FIG. 2, this treatment is repeated from the third time on, increasing the volume of plasma drawn each time as at the second time, until the volume of plasma drawn reaches the target volume of plasma exchange, 1,600 ml in this embodiment. The intervals between treatments from the third time on are also determined properly according to the condition of the patient, the volume of plasma drawn, the concentrations of ailment causing constituents, the recovery of plasma products other than ailment causing constituents, and so on. The interval is preferably longer than a week. The increment of volume of plasma drawn from the third time on must not be same and may also be changed according to the patient's condition.

Figure 2:
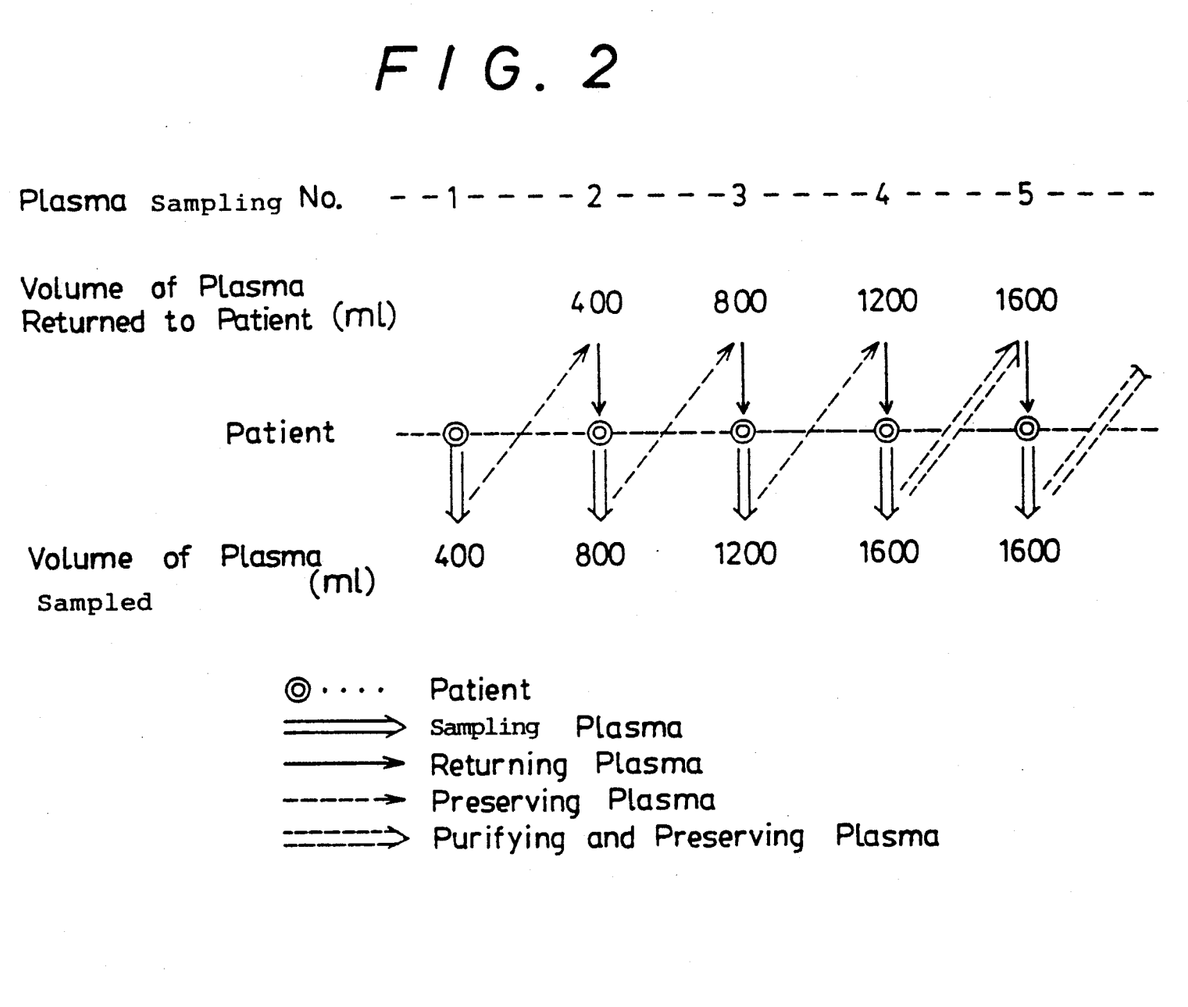
FIG. 2 is a diagram to illustrate an embodiment of the second plasma purification treatment according to the present invention.

After the volume of plasma drawn has reached the target volume of plasma exchange, that volume of plasma is drawn each time, returning the same volume of plasma drawn at the previous time and purified as shown in FIG. 2. This treatment is repeated as necessary.

Hereinafter described is an example of the present invention referring to FIG. 4.

The first drawing of plasma can be conducted by a plasma collecting circuit 1 and the plasma collecting apparatus.

The plasma collecting circuit 1 comprises a blood collection needle 21, a blood collection bag 5 having a tube 20, a first blood transportation tube 2 which connects the blood collection needle 21 to the tube 20 of the blood collection bag 5, a blood separator 7, a second blood transportation tube 6 which connects the tube 20 of the blood collection bag 5 to the blood separator 7, a third blood transportation tube 8 which connects a blood outlet of the blood separator 7 to the first blood transportation tube 2, four plasma collection bags 10a, 10b, 10c, 10d not containing salting out agent, the plasma transportation tube 9 which connects a plasma outlet of the blood separator 7 to these plasma collection bags, an anticoagulant liquid container 30 and an anticoagulant liquid transportation tube 31 which connects the anticoagulant liquid container 30 to the tube 20 of the blood collection bag 5.

In this example of the invention, 400 ml of plasma is drawn from the patient at the first drawing of plasma.

About 400 ml of plasma is collected into the plasma collection bag 10a by the plasma collecting circuit 1 and the plasma collecting apparatus. The plasma collection bag 10a is cut off from the plasma collecting circuit 1. The collected plasma is preserved about 4° C.

The second drawing of plasma is conducted after a certain period, for example at least three days, preferably at least one week, from the first drawing of plasma.

In this example of the invention, 800 ml of plasma is drawn from the patient at the second drawing of plasma. At the same time, the above preserved plasma (about 400 ml) is returned to the same patient. The second drawing of plasma can be conducted by the above mentioned plasma collecting circuit 1 and plasma collecting apparatus.

At first about 400 ml of plasma is collected into the plasma collection bag 10a, and then about 400 ml of plasma is collected into the plasma collection bag 10b. Hereby, about 800 ml of plasma is collected.

The third drawing of plasma is conducted after a certain period, for example at least three days, preferably at least one week, from the second drawing of plasma.

In this example of the invention, 1200 ml of plasma is drawn from the patient at the third drawing of plasma. At the same time, the above preserved plasma (about 800 ml) is returned to the same patient. The third drawing of plasma can be conducted by the above mentioned plasma collecting circuit 1 and plasma collecting apparatus.

At first about 400 ml of plasma is collected into the plasma collection bag 10a, then about 400 ml of plasma is collected into the plasma collection bag 10b and then about 400 ml of plasma is collected into the plasma collection bag 10c. Hereby, about 1200 ml of plasma is collected.

The fourth drawing of plasma is conducted after a certain period, for example at least three days, preferably at least one week, from the third drawing of plasma.

In this example of the invention, 1600 ml of plasma is drawn from the patient at the fourth drawing of plasma. At the same time, the above preserved plasma (about 1200 ml) is returned to the same patient. The fourth drawing of plasma can be conducted by the above mentioned plasma collecting circuit 1 and plasma collecting apparatus.

At first about 400 ml of plasma is collected into the plasma collection bag 10a containing salting out agent such as NaOH, then about 400 ml of plasma is collected into the plasma collection bag 10b containing salting out agent, then about 400 ml of plasma is collected into the plasma collection bag 10c containing salting out agent and then about 400 ml of plasma is collected into the plasma collection bag 10d containing salting out agent. Hereby, about 1600 ml of plasma is collected. 1600 ml of plasma is a predetermined target volume of plasma exchange. The collected plasma is mixed with the salting out agent in the plasma collection bag. The collected plasma is preserved below 4° C. Causative constituents such as high molecular weight proteins in plasma precipitate by the difference of solubility in the plasma collection bags.

The fifth drawing of plasma is conducted after a certain period, for example at least three days, preferably at least one week, from the fourth drawing of plasma.

Before the fifth drawing of plasma, the collected plasma in the plasma collection bags 10a, 10b, 10c and 10d is treated by the plasma treatment apparatus 60 shown in FIG. 5.

1600 ml of plasma is drawn from the patient at the fifth drawing of plasma. At the same time, the above treated plasma (about 1600 ml ) is returned to the same patient. The fifth drawing of plasma can be conducted by the above mentioned plasma collecting circuit 1 and plasma collecting apparatus.

At first about 400 ml of plasma is collected into the plasma collection bag 10a, then about 400 ml of plasma is collected into the plasma collection bag 10b, then about 400 ml of plasma is collected into the plasma collection bag 10c and then about 400 ml of plasma is collected into the plasma collection bag 10d. Hereby, about 1600 ml of plasma is collected. The plasma collection bag 10a, 10b, 10c and 10d are cut off from the plasma collecting circuit 1. The collected plasma is mixed to the salting out agent in the plasma collection bag. The collected plasma is preserved above 4° C.

Before the fifth drawing of plasma, the collected plasma in the plasma collection bags is treated by a plasma treatment apparatus shown in FIG. 5.

After the fifth drawing of plasma, the above treatment and drawing of plasma are repeated as necessary.

Next, an embodiment of the second plasma purification treatment according to the present invention is described below referring to FIG. 3.

Next, an embodiment of the second plasma purification treatment according to the present invention is described below referring to FIG. 4.

The second plasma purification treatment of the type wherein blood is drawn from a patient, the blood is separated plasma and concentrated cellular elements, the concentrated cellular elements are returned to the patient, the plasma treated to remove ailment causing constituents and thereafter the treated plasma is returned to the patient;

the improvement wherein an increased volume of plasma becomes available for the extracorporeal plasma treatment;

comprising the steps, (a) sampling a first sample of plasma from the patient, said sample of the plasma having a first volume which is up to about 12% of the total volume of blood circulating in the patient, and storing the first sample of the plasma, under conditions to preserve its properties; thereafter (b) waiting a time sufficient for the patient's body to replace substantially the sampled plasma; thereafter (c) sampling a second sample of plasma from the patient, said sample of the plasma having a volume which is up to about 12% of the total volume of blood circulating in the patient, and storing the second sample of plasma, under conditions to preserve its properties; thereafter (d) the steps of the sampling, storing and waiting are continued until a predetermined target volume of the plasma is sampled from the patient (e) returning the sampled and preserved plasma to the patient and taking the target volume of the plasma is available as an extracorporeal supply.

When applying this second plasma purification treatment according to the present invention to a patient, a target volume of plasma exchange is determined before starting treatment taking into consideration the weight, age, and disease state of the patient, ailment causing constituents, concentrations of the ailment causing constituents, and so on. Thereafter, an appropriate volume of plasma within 12% of the patient's whole circulating blood, 400 ml for example, is drawn from the patient into a sterile container as the first drawing.

The first operation is only this sampling of plasma and therefore the patient has to be put under restraint only for the time necessary for drawing plasma.

Plasma is separated from the blood by conventional methods such as centrifugation with a centrifugal or filtration with membrane filter. The sampled plasma is preserved with or without the purification. The sampled plasma is preferably preserved after being purified. It is preferable to preserve the plasma by cooling below 4° C. This cold preservation prevents the denaturation and loss of activity of plasma components. Frozen preservation is more preferable for cold preservation. Ailment causing constituents in plasma can be removed by the same methods as for the first plasma purification method according to the present invention.

The second sampling of plasma is conducted after a certain period, 2 to 30 days for example, from the first sampling. The certain period is preferably three days up to thirty days, more preferably at one week. An appropriate volume of plasma within 12% of the patient's whole circulating blood is sampled by this second sampling as by the first sampling. In this embodiment, the same 400 ml of plasma is sampled as shown in FIG. 3. The sampled plasma is preserved after being purified. This sampling of plasma is repeated until the total volume of preserved plasma reaches the target volume of plasma exchange, for example, 1600 ml.

The sampled plasma may also be preserved without the purification treatment and purified at once after the target volume of plasma is collected.

The intervals between treatments from the third sampling of plasma on are also determined properly according to the condition of the patient. The interval is preferably longer than a week. The sampling volume of plasma from the third sampling of plasma on need not be same and may also be changed according to the patient's condition.

Figure 3:
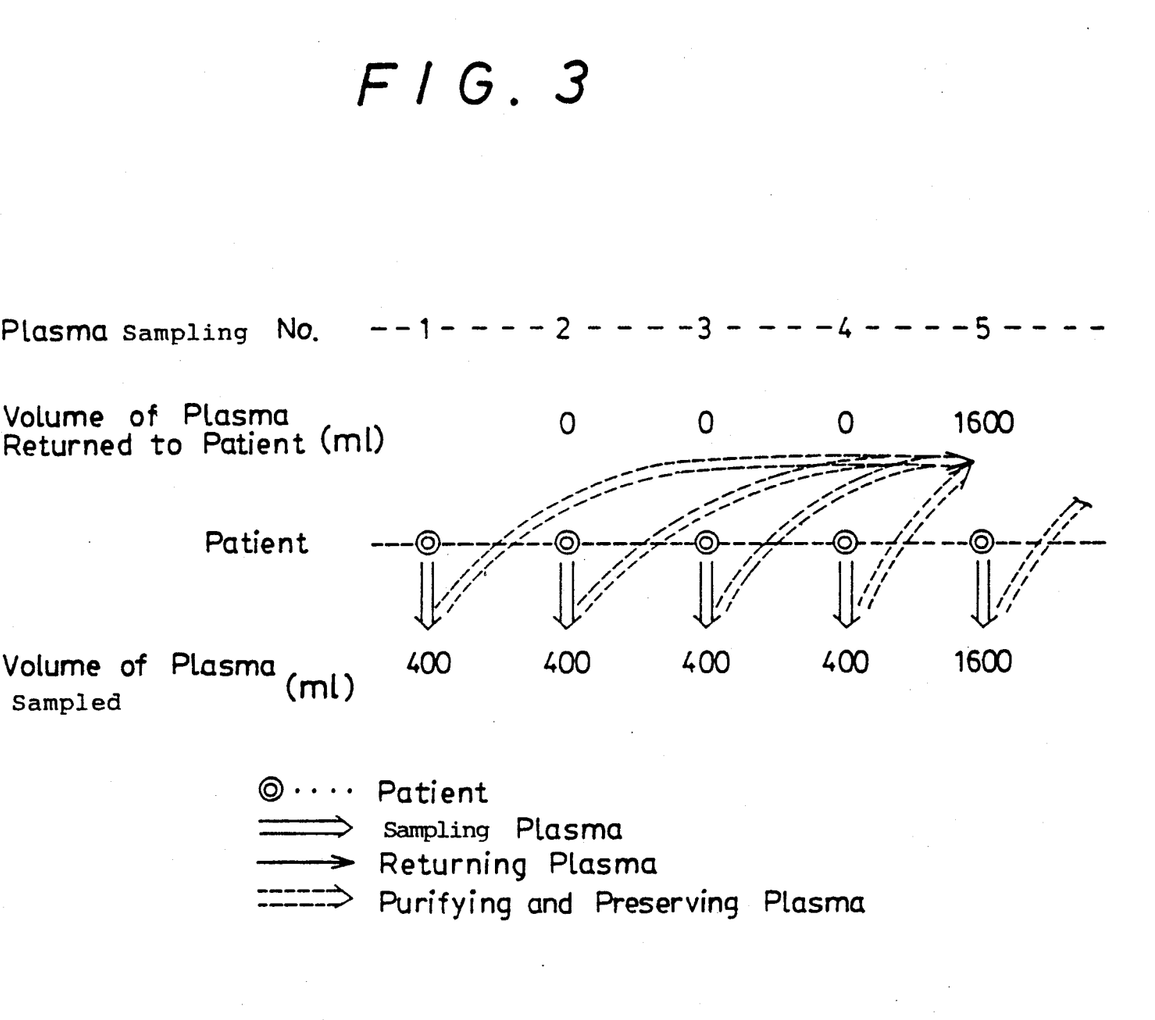
FIG. 3 is a diagram to illustrate an embodiment of the third plasma purification treatment of the present invention.

Thereafter, the target volume of plasma is sampled and the same volume of purified plasma is returned as in FIG. 3.

Although the plasma preserved to collect the target volume is also returned to the patient after having been purified in this embodiment, it may be returned without the purification treatment until the volume of the preserved plasma reaches the target volume.

The plasma purification treatment according to the present invention is ended concerning to a recovery condition of the patient.

It is preferable that the plasma purification treatment is ended gradually and decreasing the volume of plasma exchanged.

Further, it is preferable to conduct the plasma purification treatment in an aseptic condition. A method to meet this requirement is sampling plasma into a sterile sealed container (a soft-resin bag, for example), connecting the bag to a plasma purifying apparatus, receiving the purified plasma into another sealed container (a soft-resin bag, for example) connected to the plasma purifying apparatus, and then returning the purified plasma from the bag to the patient at the next treatment.

Hereinafter described is an example of the present invention referring to FIG. 3.

The first sampling of plasma can be conducted by a plasma collecting circuit 1 and the plasma collecting apparatus.

The plasma collecting circuit 1 comprises a blood collection needle 21, a blood collection bag 5 having a tube 20, a first blood transportation tube 2 connecting the blood collection needle 21 to the tube 20 of the blood collection bag 5, a blood separator 7, a second blood transportation tube 6 connecting the tube 20 of the blood collection bag 5 to the blood separator 7, a third blood transportation tube 8 connecting a blood outlet of the blood separator 7 to the first blood transportation tube 2, four plasma collection bags 10a, 10b, 10c, 10d containing salting out agent, the plasma transportation tube 9 connecting a plasma outlet of the blood separator 7 to these plasma collection bags, an anticoagulant liquid container 30 and an anticoagulant liquid transportation tube 31 connecting the anticoagulant liquid container 30 to the tube 20 of the blood collection bag 5.

In this example of the invention, 400 ml of plasma is sampled from the patient at the first sampling of plasma.

About 400 ml of plasma is collected into the plasma collection bag 10a by the plasma collecting circuit 1 and the plasma treatment apparatus. Then the plasma collection bag 10a is cut off from the plasma collecting circuit 1. The collected plasma is mixed to the salting out agent in the plasma collection bag. The collected plasma is preserved below 4° C.

The second sampling of plasma is conducted after a certain period, for example at least three days, preferably at least one week, from the first sampling of plasma.

In this example of the invention, 400 ml of plasma is sampled from the patient at the second sampling of plasma. About 400 ml of plasma is collected into the plasma collection bag 10a by the plasma collecting circuit 1 and the plasma collecting apparatus.

The third sampling of plasma is conducted after a certain period, for example at least three days, preferably at least one week, from the second sampling of plasma.

In this example of the invention, 400 ml of plasma is sampled from the patient at the third sampling of plasma. About 400 ml of plasma is collected into the plasma collection bag 10a by the plasma collecting circuit 1 and the plasma collecting apparatus.

The fourth sampling of plasma is conducted after a certain period, for example at least three days, preferably at least one week, from the third drawing of plasma.

In this example of the invention, 400 ml of plasma is drawn from the patient at the fourth sampling of plasma. About 400 ml of plasma is collected into the plasma collection bag 10a by the plasma collecting circuit 1 and the plasma collecting apparatus. The total volume of the collected plasma reaches a predetermined target volume (1600 ml) of plasma exchange.

The fifth sampling of plasma is conducted after a certain period, for example one week, from the fourth sampling of plasma.

Before the fifth sampling of plasma, the collected plasma in the plasma collection bags is treated by the plasma treatment apparatus 60.

1600 ml of plasma is sampled from the patient at the fifth sampling of plasma. At the same time, the above treated plasma (about 1600 ml) is returned to the same patient. The fifth sampling of plasma can be conducted by the above mentioned plasma collecting circuit 1 and plasma collecting apparatus.

About 400 ml of plasma is collected into the plasma collection bag 10a containing salting out agent such as NaOH, about 400 ml of plasma is collected into the plasma collection bag 10b containing salting out agent, about 400 ml of plasma is collected into the plasma collection bag 10c containing salting out agent and about 400 ml of plasma is collected into the plasma collection bag 10d containing salting out agent. Hereby, about 1600 ml of plasma is collected. After that, the plasma collection bag 10a, 10b, 10c and 10d are cut off from the plasma collecting circuit 1. The collected plasma is mixed to the salting out agent in the plasma collection bag. The collected plasma is preserved above 4° C.

After the fifth sampling of plasma, the above treatment and sampling of plasma are repeated as necessary.

The plasma purification treatment of the present invention is risk free from infection, since it uses purified patient's own plasma for plasma exchange and hence does not need substitute plasma as described above.

Further, patients have to be put under restraint only for a considerably shorter time required for drawing plasma and returning purified plasma. The time is further made shortened by conducting sampling of plasma and returning of purified plasma.

Furthermore, since the plasma purification treatment of the present purifies plasma off-line, it does not need a shunt circuit and connection of thick catheters as required in an on-line purification treatment to allow a sufficient blood stream into an extracorporeal circuit. Therefore, it greatly decreases the stress suffered by patients and does not need a costly apparatus for extracorporeal circulation and on-line treatment.

Moreover, the plasma purification treatment of the present invention can be carried out easily and without risk by people who have a basic knowledge of blood transfusion but do not have an expert knowledge of extracorporeal circulation.

What is claimed is:

1. In extracorporeal plasma purification treatment of the type wherein blood is drawn from a patient, the blood is separated into plasma and concentrated cellular elements, the concentrated cellular elements are returned to the patient, the plasma is treated to remove ailment causing constituents and thereafter the treated plasma is returned to the patient;

the improvement wherein an increased volume of plasma becomes available for the extracorporeal plasma treatment;

comprising the steps, (a) sampling a first sample of plasma from the patient, said sample of the plasma having a first volume which is 1% to about 12% of the total volume of blood circulating in the patient, and storing the first sample of the plasma, under conditions to preserve its properties; thereafter (b) waiting a time sufficient for the patient's body to replace substantially the sampled plasma; thereafter (c) returning the first sample of plasma to the patient and taking a second sample of plasma having a second volume which is equal to the sum of the first volume and an additional amount of 1% to 12% of the volume of blood circulating in the patient; whereby the second volume of the plasma is available as an extracorporeal supply.

2. The treatment of claim 1, wherein the plasma is treated to remove ailment causative constituents before returning the plasma to the patient.

3. The treatment of claim 1, in which the volume of plasma sampled from the patient at each time is changed according to a condition of the patient.

4. The treatment of claim 1, in which the sampled plasma is preserved below 4° C. before the purification treatment.

5. The treatment of claim 1, in which the treated plasma is preserved below 4° C.

6. The treatment of claim 1, wherein the steps of returning plasma previously sampled from a patient, followed by sampling an amount of plasma greater by 1% to about 12% of the patient's total blood volume than the amount of plasma returned to the patient, and storing the plasma, are continued until a predetermined target volume of plasma is sampled from the patient.

7. The treatment of claim 6, wherein the plasma is treated to remove ailment causative constituents before returning the plasma to the patient.

8. The treatment of claim 6, in which said target volume of plasma is changed according to the condition of the patient.

9. The treatment of claim 6, wherein after the target volume is reached, the steps of sampling of plasma and returning plasma are continued at the target volume, and the plasma is treated to remove ailment causative constituents before returning the plasma to the patient.

10. The treatment of claim 9, wherein the time between sampling the plasma and returning the plasma for each sampling of plasma is at least three days.

11. The treatment of claim 9, wherein the time between sampling the plasma and returning the plasma for each sampling of plasma is at least one week.

12. The treatment of claim 9, wherein the time between sampling the plasma and returning the plasma for each sampling of plasma is three days up to thirty days.

13. In extracorporeal plasma purification treatment of the type wherein blood is drawn from a patient, the blood is separated into plasma and concentrated cellular elements, the concentrated cellular elements are returned to the patient, the plasma is treated to remove ailment causing constituents and thereafter the treated plasma is returned to the patient;
the improvement wherein an increased volume of plasma becomes available for the extracorporeal plasma treatment;
comprising the steps,
(a) sampling a first sample of plasma from the patient, said first sample of the plasma having a first volume which is 1% to about 12% of the total volume of blood circulating in the patient, and storing the first sample of the plasma, under conditions to preserve its properties; thereafter
(b) waiting a time sufficient for the patient's body to replace substantially the sampled plasma; thereafter
(c) sampling a second sample of plasma from the patient, said second sample of the plasma having a volume which is 1% to about 12% of the total volume of blood circulating in the patient, and storing the second sample of plasma, under conditions to preserve its properties; thereafter
(d) the steps of the sampling, storing and waiting are continued until a predetermined target volume of the plasma is sampled from the patient
(e) returning the sampled and preserved plasma to the patient and taking the target volume of the plasma is available as an extracorporeal supply.

14. The treatment of claim 13, wherein the plasma is treated to remove ailment causative constituents before returning the plasma to the patient.

15. The treatment of claim 13, wherein the steps of sampling and returning the plasma are continued at the target volume, the step of waiting is continued, and plasma is treated to remove ailment causing constituents before returning the plasma to the patient.

16. The treatment of claim 15, wherein the plasma is treated to remove ailment causative constituents before returning the plasma to the patient.

17. The treatment of claim 15, wherein the time between sampling the plasma and returning the plasma for each sampling of plasma is at least three days.

18. The treatment of claim 15, wherein the time between sampling the plasma and returning the plasma for each sampling of plasma is at least one week.

19. The treatment of claim 15, wherein the time between sampling the plasma and returning the plasma for each sampling of plasma is three days up to thirty days.

20. The treatment of claim 15, in which the volume of plasma sampled from the patient at each time is changed according to a condition of the patient.

21. The treatment of claim 15, in which said target volume of plasma is changed according to the condition of the patient.

22. The treatment of claim 15, in which the sampled plasma is preserved below 4° C. before the purification treatment.

23. The treatment of claim 15, in which the treated plasma is preserved below 4° C.

* * * * *